United States Patent [19]

Khuri

[11] Patent Number: 5,352,411
[45] Date of Patent: Oct. 4, 1994

[54] DEVICE FOR DETERMINATION OF TEAR CONSTITUENTS

[76] Inventor: Raja N. Khuri, 122 Longmeadow Rd., Greenville, N.C. 27858

[21] Appl. No.: 106,282

[22] Filed: Aug. 13, 1993

[51] Int. Cl.$^5$ .............................................. G01N 21/00
[52] U.S. Cl. ...................................... 422/58; 422/61
[58] Field of Search ................. 128/760, 771; 422/56, 422/58, 61

[56] References Cited

U.S. PATENT DOCUMENTS 4,994,751  2/1991  Cook et al. ......................... 128/771

OTHER PUBLICATIONS

Thaysen J. H. and N. A. Thorn, Excretion of Urea, Sodium, Potassium and Chloride in Human Tears, Amer. J. Physiol 178:160–164 (1954).
Uotila, M. H., R. E. Soble, and J. Savory, Measurement of tear calcium levels, Invest. Ophthalmol. 11:258–259 (1972).
Avisar, R., H. Savir, Y. Sidi, and J. Pinkhas, Tear Calcium and magnesium levels of normal subjects and patients with hypocalcemia or hypercalcemia, Invest. Ophthamol. 16:1150–1151 (1977).
Van Haeringen, N. J. and E. Glasius, Collection Method Dependent Concentrations of Some Metabolites in Human Tear Fluid, with Special Reference to Glucose Hyperglycaemic Conditions, Albrecht von Graefes Arch. Klin. Ophthmol. 202:1–7 (1977).
Van Haeringen, N. J., Clinical Biochemistry of Tears, published 1981.
Desai, B. M., and B. C. Lavingia-Ahmedabad. Cornea Thickness and Tear Glucose Levels in Diabetes Millitus and Normal Persons, Ind. J. Ophth. 35:130–132 (1987).
Romano, A. and F. Rolant, A Non-Invasive Method of Blood Glucose Evaluation by Tear Glucose Measurement, for the Detection and Control of Diabetic States, Metabolic, Pediatric and Systemic Ophthamol. 11:78–80 (1988).
Kang, J., G. Fulop and A. H. Friedman, Tear urea nitrogen and creatinine levels in renal patients, Acta Ophthalmol. 66:407–412 (1988).
Rolando, M., F. Baldi, and G. Calabria, Tear Mucus Crystallization in Children with Cystic Fibrosis, Oppthalmologica 197:202–206 (1988).
Maurice, D., The Charles Prentice Award Lecture 1989: The Physiology of Tears, Optometry and Vision Science 67:391–399 (1990).

Primary Examiner—Lyle A. Alexander
Attorney, Agent, or Firm—Olive & Olive

[57] ABSTRACT

A device for determination of a tear constituent, including an absorbent tear strip wick and an electrochemical strip connected to one end of the wick. The electrochemical strip is impregnated with an indicator chemistry. The device may be used to detect organic and ionic constituents in tears by placement of the free end of the tear strip wick in the corner of the eye, and after tear absorption by the device, determining changes in the chemistry of the device associated with the particular constituent.

1 Claim, 1 Drawing Sheet

DEVICE FOR DETERMINATION OF TEAR CONSTITUENTS

BACKGROUND OF THE INVENTION

1. Field of the Invention

This invention relates generally to methods and devices used for determination of analytes in bodily fluids, and in particular, pertains to a sensor strip for determination of organic and ionic constituents in tears. Analyzing the constituents of tears lends itself to frequent home monitoring because of the non-invasiveness of the method.

2. Description of the Related Art

Bodily fluids such as blood are often analyzed for trace constituents as being symptomatic of the physiological and medical health of patients. Obtaining blood for the tests, however, is an invasive measure requiring arterial or venous puncture, which is preferably avoided. The means of analysis of these bodily fluid vary, and include various analytical devices and electrometric measurement means. The constituents found in tears are representative of those found in the blood supply to the brain, because the palpebral conjunctiva is supplied by the ophthalmic artery, a branch of the internal carotid artery, a major supplier of the brain. Although tears are an alternative body fluid which can be analyzed, it is generally difficult or impossible to obtain a large enough tear sample to allow measurement or detection of constituents. To obtain such a volume of tears for research or analysis, investigators have generally been required to use artificial stimulation of tear production, for example, with tear-inducing chemicals, fans, and the like. The concentration of some solutes in tears is flow-dependent and therefore depends on the method of collection of the tears.

Schirmer tear strips (SNO*STRIPS TM ) can be ordered from Smith and Nephew Pharmaceuticals (Romford, England). The Schirmer tear strips are sterile tear flow test strips (60 mm × 5 mm) cut off from Whatman (no.41) filter paper absorbent material. The strips are folded 5 mm from the rounded end, and the folded end is inserted into the inferior conjunctival sac at the junction of the middle and temporal thirds of the eyelids. The subject closes the eyes lightly for five minutes and the strips are removed and the extent of wetting is measured from the fold.

The method and device of the invention allows determination of such organic tear constituents such as glucose, urea, and ketone bodies, as well as the determination of ionic tear constituents such as potassium, magnesium and calcium. The need for determination of these constituents, as well as previous monitoring techniques, are discussed below.

Glucose. The glucose concentration of tears remains invariant until the blood sugar exceeds the threshold level. When the level of plasma glucose rises to 200 mg/dl or 10 mM it may be correlated with the hyperglycemic elevated levels, and tear glucose can be used as an index for blood glucose concentration. See, Van Harringen et al., Albret von Graefes Arch. Klin. Ophthalmol. 202:1, 1977). The method of the invention allows home monitoring of glucose in the tear fluid as a substitute for fractional urine glucose determination as a method of guiding insulin therapy in diabetes mellitus.

Urea. The concentration of urea in tears (TUN) has been shown to be in close agreement with the simultaneous blood values of urea nitrogen (BUN), implying an unrestricted passage of the urea molecule through the blood-tear barrier in the lacrimal gland. Therefore, TUN can be monitored non-invasively as a substitute for BUN. The method of the invention allows assessment, in a clinical or other setting, of the adequacy of dialysis (both hemodialysis and peritoneal dialysis) in end-stage renal disease, as well as monitoring the development of uremia as the patient progresses from renal insufficiency to renal failure.

Ketone bodies. Free fatty acids from adipose tissue stores are the source of ketone bodies. Ketosis or ketogenesis is the process of ketone body formation. Ketogenesis is stimulated by glucagon excess and insulin lack as in diabetic keto acidosis (DKA). Ketone bodies appear in blood and urine in DKA and starvation. In DKA treatment they disappear from the urine early. The end point for correction of DKA is the disappearance of ketone bodies from the blood. Tears, which are more representative of the environment of the brain than is systemic blood is the ideal non-invasive fluid to monitor for ketone body appearance and disappearance. Currently, ketone bodies are determined semi-quantitatively in the blood or urine by reagent test strips (for example, KETOSTIX TM , made by Ames, Division of Miles Laboratories). Ketone bodies are also determined by ACETEST TM tablets (manufactured by Ames, Division of Miles Laboratories) which are made of glycine, Na-nitroprusside, $Na_2$, $PO_4$, and lactose, are dissolved in the fluid to be tested. A positive result with these tablets yields a lavender purple color when the concentration of ketone bodies is greater than or equal to 5-10 mg%.

Potassium ion. Potassium disorders range from hyperkalemia to hypokalemia, and are second only to hydrogen ion disorders as causes of mortality and morbidity. Hyperkalemia is the most dangerous and lethal electrolyte disorder and constitutes a common cause of sudden death on account of fatal cardiac arrhythmias, but may be reversed if appropriate measures are taken in time. Hyperkalemia, in which the serum $K^+$ concentration is greater than 5.5 mM/l can be caused by excessive potassium intake, inadequate $K^+$ excretion or a shift of $K^+$ from the tissues to extracellular fluid (ECF). There are a number of commonly used drugs which contribute to the latter two causes. The heart is very sensitive to changes in serum $K^+$, and is effectively a bio-sensor for extracellular $K^+$ levels. With hyperkalemia, cardiac excitability increases, which is reflected in EKG changes which have some correlation with the $K^+$ level.

Hypokalemia, in which the serum $K^+$ level is less than 3.5 mM/l, is often associated with $K^+$ depletion. Hypokalemia and $K^+$ depletion can be caused by inadequate $K^+$ intake, excess renal $K^+$ excretion, excessive gastrointestinal (GI) $K^+$ loss by vomiting or diarrhea, and a shift of $K^+$ into cells and tissues. The clinical manifestations of hypokalemia are cardiac (predisposition to digitalis intoxication and irregular heartbeats), hemodynamic (decrease in blood pressure), neuromuscular weakness and paralysis of GI and striated/skeletal muscle, renal (inability to concentrate urine progressing to renal diabetes insipidus), and endocrine (decrease in renin and aldosterone, and decrease in insulin secretion with carbohydrate intolerance of diabetes).

Though the instantaneous determination (STAT) of serum $K^+$ has saved lives, many crises are missed due to the lack of a non-invasive, monitoring system which is easily used and may be used at home. Tears contain about 15–30 milliequivalents (mEq) of $K^+$ per liter, which is about 3–6 times the level of serum $K^+$, with an average level in serum being about 4.5 mEq/liter. This indicates that there is active secretion of $K^+$ in tears (Thaysen et al., Am. J. Physiol. 178:160, 1954; Miller, Am. J. Opthalmol. 47:773, 1970).

Calcium and Magnesium. Blood plasma is quite different from the interstitial fluid that bathes the cells directly. Plasma is a colloidal solution while interstitial fluid is a simple crystalloid solution. Blood plasma is continuously stirred and agitated and mixed with an almost equal volume of mostly charged red blood cells. Electrometric determination of ionic activity in plasma, which is a currently widely accepted method of determining $Ca^{2+}$, is problematic, first, due to plasma proteins, because of a phenomenon known as residual liquid junction at the tip of the reference electrode when it measures a constituent of plasma against simple crystalloid standard solutions, and second, due to the sedimentation of charged red blood cells in whole blood due to the influence of gravity.

Because tears do not have plasma proteins, they are closer to interstitial fluids than plasma. Interstitial fluid calcium is critical for a variety of functions especially neuromuscular excitability and irritability. Low free $Ca^{2+}$ and $Mg^{2+}$ cause convulsions and tetany. In addition, low $Ca^{2+}$ levels are commonly seen in conditions of low plasma proteins in newborns and alkalosis. Magnesium deficiency may be associated with normo-calcemic or hypocalcemic states, as well as with hyperirritability, tetany, convulsions and EKG changes, and is often associated with $K^+$ deficiency.

Magnesium and calcium in blood plasma occur in three forms: (1) free ions; (2) diffusible complexes; and (3) protein-bound. One-half of the calcium is protein-bound, while ⅓ of the total magnesium is protein-bound, with most of the remaining calcium and magnesium being ionic $Ca^{2+}$ and $Mg^{+2}$, and the complexes being only a few percent.

Thus, an electrometric determination of ionic $Ca^{2+}$ and $Mg^{+2}$ in tears is more reliable than in plasma, and correlates better with clinical neuromuscular irritability, in view of the effect of proteins on the residual liquid junction and the low (about 0.3) activity coefficient of the solution (activity coefficient being defined as the activity divided by the concentration). Total calcium and magnesium, as opposed to ionic calcium and magnesium, correlate poorly with neuromuscular irritability. Thus, in tears, measurement of these two divalent cations electrometrically is advantageous because there is no protein binding, no liquid junction effect, no sedimentation effect, and more confidence in activity coefficients, and tears reflect more closely the fluid environment of the brain through supply by the carotid. Typical concentrations of $Ca^{2+}$ in tears are 0.4–0.8 mM (as compared to 1.09–1.33mM in plasma) and of $Mg^{2+}$ in tears are 0.5–1.1 mM (as compared to 4.36–5.32 mg % in plasma). See Uotila et al., Invest. Ophthalmol. 11:258, 1972; Avisar et al., Invest. Ophthalmol. 16:1150, 1977.

It is therefore an object of the invention to provide a non-invasive method and device for obtaining tears, and for analyzing the tears for constituents.

It is another object of this invention to provide a method and device which maintains a constant flow of tears, driven by the constancy of the capillarity forces of a wick.

It is a further object of this invention to provide a method and device having embodiments which may be graded either semiquantitatively or quantitatively.

It is a further object of the invention to provide a non-invasive method and device which may use in the home or other non-clinical settings for the determination of organic and ionic constituents in tears.

Other objects and advantages will be more fully apparent from the following disclosure and appended claims.

SUMMARY OF THE INVENTION

The invention comprises a method, device and kit for determination of tear constituents. The device includes an absorbent tear strip wick and an electrochemical strip connected to one end of the wick. The electrochemical strip is impregnated with sensor and indicator chemistry. Depending on the indicator and sensor chemistry, the device may be used to detect a particular organic or ionic constituent in tears by placement of one end of the tear strip wick in the corner of the eye, and after tear absorption by the device, determining changes in the chemistry of the device associated with the particular constituent.

Other aspects and features of the invention will be more fully apparent from the following disclosure and appended claims.

DETAILED DESCRIPTION OF THE INVENTION AND PREFERRED EMBODIMENTS THEREOF

Figure 1:
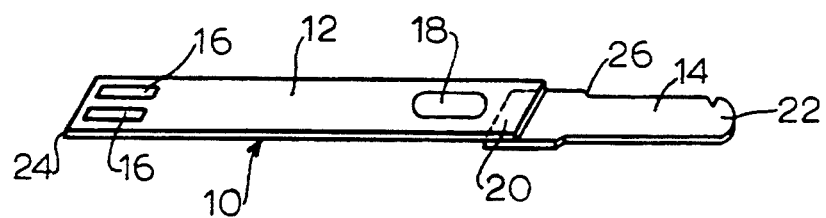
FIG. 1 is an upper perspective view of a tear strip according to the invention.

The invention includes a method and device for determination of organic and ionic tear constituents, as well as a kit containing said device which may be used in the method of the invention. The kit may, in addition to the device, include, for example, instructional materials for home or other use, and semi-quantitative color charts for comparison of colorimetric results.

The electrochemical or colorimetric tear strip 10 of the invention (FIG. 1) comprises a portion 14 of a Schirmer-type tear strip attached to a blood electrochemical test strip portion 12 as is used for blood analysis for the particular component to be measured in tears with the invention.

In general, the electrochemical test strip portion 12 used in the invention may either contain one or more reactants involving a chromogen which indicates the presence of the particular component, or may contain a substance measurable by ion-selective electrodes (sensing ions with ionic or electro-neutral sensors) or by enzymatic reactions (employing enzymes or electrochemical sensors based on either amperometric or polarographic reactions where current flow is measured or potentiometric reactions where voltage is measured as is known in the art.

The preferred electrochemical test strip portion 12 for use in the invention is a matrix to which a sensor is bound. As shown in FIG. 1, a typical electrochemical test strip portion 12 used in the invention contains an electro-chemical sensing area 16, and a blood well 18 (which in the invention becomes a tear well).

In particular, a preferred sensor for glucose comprises glucose oxidase. The preferred sensor for urea comprises urease. For ketone bodies the reaction is based on an amperometric oxidation-reduction. For potassium the preferred sensor comprises valinomycin. For calcium and magnesium organophosphate salts are used as sensors, for example, di-p-octylphenyl phosphate is used for calcium.

To prepare the tear strip 10 of the invention, a Schirmer tear strip, having dimensions of about 50 mm×5 mm, and a shoulder area 26 about 15 mm from a one rounded end, is cut some 20 mm from the rounded end and glued (using a glue such as Elmer's TM glue) to the blood sampling end 20 of the electrochemical test strip portion 12. A standard Schirmer tear strip has an indentation on one side to assist in sampling the tears, which is optionally part of the tear strip 10 of the invention as well.

In the method of use of the invention, after applying a drop of a local anesthetic (ACTANE TM made by Alkorn, Inc., Los Angeles, Calif.) to the conjunctiva, the rounded end 22 of the Schirmer wick portion 14 of the strip 10 is applied to the lateral bulbar conjunctiva in the same manner as known in the art, the electrochemical strip proper 12 is fixed to the temple skin with adhesive, the eyes are closed, and 5-10 minutes are allowed for tear flow by capillarity to soak the wick portion 14 and then the test strip portion 12. The results are read, preferably using a reader sensitive to the colorimetric or electrometric results tested by the electrochemical test strip 12, and may generally be the same reader as is used for determination of the concentration of the particular component in blood. The free end 24 of the electrochemical test strip portion of the invention is inserted into the companion reader for the particular chemical component, and the reading is taken using methods provided by the manufacturer of the reader. Prior to utilizing a reader for a tear sample, the reader is calibrated according to the reader manufacturer's instructions and the proper controls for each component are used.

The particular tear constituent which a specific tear strip may be used for depends on the chemistry applied to the strip. As test strips for different constituents of blood become available to the public, these test strips may be attached to Schirmer strips according to the invention herein and may be read using readers developed for the particular blood strips.

Where there is knowledge of the particular chemistry and ionic reactions associated with particular tear components tear strips according to the invention may be developed even if blood test strips have not yet been developed for that component in the blood, utilizing standard methods of impregnating fibrous material, attaching sensors and indicators, and the like. Similarly, choice of appropriate indicators for analysis of a new component allows use of readers already available for other analytes for which the same or similar indicators have been used.

The features and advantages of the present invention will be more clearly understood by reference to the following examples, which are not to be construed as limiting the invention.

EXAMPLES

EXAMPLE I

Glucose tear strip

For the glucose tear strip, an enzymic strip, such as that manufactured under the trade name EXAC-TECH ® (MediSense, Inc., Waltham, Mass.) is used, which is impregnated with the glucose oxidase enzyme. In the invention, the enzymic strip is attached to the Schirmer strip by a glue such as Elmer's TM glue. Presence of glucose is determined by inserting the end of the strip into a calibrated COMPANION TM reader provided with the enzymic strip for measuring the component in the blood. A button is pressed and the reading is taken. Other glucose-indicating strips are made by Boehringer-Mannheim, Ames (Division of Miles) and Life Scan (Division of Johnson & Johnson). These strips are read by other methods specified by the company which manufactures the strips.

EXAMPLE II

Urea tear strip

For the urea tear strip, an enzymic strip, such as that recently developed by MediSense, Inc. (Waltham, Mass.) is used, which is impregnated with urease. This enzymic strip is attached to the Schirmer strip by a glue as in the other embodiments. Presence of urea is determined by the reader provided for the urease enzymic strip by MediSense, Inc., utilizing the method of quantitation utilized for quantitation of urease in blood.

EXAMPLE III

Ketone body tear strip

For the ketone body tear strip, an indicator strip marketed for ketone bodies and utilizing amperometric oxidation-reduction reactions may be used. Such a strip utilized for quantitation of ketone bodies in blood has been developed by Medisense, and utilizes the same reader as for blood glucose. The same reader and strip can be used for measurement of ketone bodies in tears, as the concentrations of ketone bodies in tears and in plasma are equivalent.

EXAMPLE IV

Potassium ion tear strip

For the potassium ion strip, valinomycin is immobilized on the tear strip as a sensor of the K+. MediSense has also developed a sensor strip for the potassium ion and an appropriate reader which may be used in this embodiment of the invention. This strip may be used at home in a qualitative or semi-quantitative way, or may be used more quantitatively in the hospital with an appropriate reader. Alternatively, the near infrared spectra of the immobilized valinomycin may be used to quantitate the K+ level.

EXAMPLE V

Calcium and magnesium tear strips

An indicator strip containing organo-phosphate salts is used as the sensor for ionic calcium or magnesium using known reaction mechanisms for electrometric detection of these components.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

REFERENCES

1. Van Harringen NJ, Glasius E. Collection method dependent concentrations of some metabolites in human tear fluid with special reference to glucose in hyperglycemic conditions. Albret yon Graefes Arch. Klin. Ophthmol. 202:1 (1977).
2. Thaysen J. H., Thorn N. A. Excretion of urea, sodium, potassium and chloride in human tears. Am. J. Physiol. 178:160 (1954).
3. Miller R. B. Tear concentrations of sodium and potassium during adaptation to contact lenses. II. Potassium observations. Am. J. Ophthalmol. 47:773 (1970).
4. Uotila M. H., Sobb R. E., Savory. Measurement of tear calcium levels. Invest. Ophthalmol. 11:258 (1972).
5. Avisar R. Sarri H., Sidi Y., Pinkhas J. Tear calcium and magnesium levels in normal subjects, and patients with hypocalcemia and hypercalcemia. Invest. Ophthalmol. 16:1150 (1977).

What is claimed is:

1. A device for determination of a tear constituent selected from the group consisting of glucose, urea, potassium, and calcium comprising:
   (a) an absorbent tear strip extending between a distal end for placement in a lateral bulbar conjunctiva of an eye of a person, and a proximal end, said tear strip having a length and width to enable the tear strip distal end to be placed in a lateral bulbar conjunctiva and to enable tear material absorbed by the tear strip distal end to migrate to the tear strip proximal end; and
   (b) an electrochemical strip extending between a distal end and a proximal end, said electrochemical strip being impregnated with sensor and indicator chemistry which in the presence of the selected constituent acts as a specific sensor of the selected constituent in tear material, said chemistry being located in an electrochemical sensing area between the distal end and the proximal end of the electrochemical strip; said electrochemical strip distal end being bonded to the tear strip proximal end in a manner enabling tear material reaching said tear strip proximal end to migrate from the tear strip proximal end to the electrochemical sensing area, thereby enabling said selected tear constituent to be detected in the electrochemical sensing area by use of a reader when the presence of the selected constituent is indicated by said chemistry.

* * * * *